(12) United States Patent
Govari et al.

(10) Patent No.: US 9,757,189 B2
(45) Date of Patent: Sep. 12, 2017

(54) PREVENTION OF KINKS IN CATHETER IRRIGATION TUBES

(75) Inventors: Assaf Govari, Haifa (IL); Ariel Garcia, Duarte, CA (US)

(73) Assignee: Biosense Webster, Inc.

( * ) Notice: Subject to any disclaimer, the term of this patent is extended or adjusted under 35 U.S.C. 154(b) by 1076 days.

(21) Appl. No.: 12/327,321

(22) Filed: Dec. 3, 2008

(65) Prior Publication Data

US 2010/0137837 A1    Jun. 3, 2010

(51) Int. Cl.
*A61B 18/14* (2006.01)
*A61M 25/00* (2006.01)
*A61B 18/00* (2006.01)

(52) U.S. Cl.
CPC ....... *A61B 18/1492* (2013.01); *A61M 25/005* (2013.01); *A61M 25/0009* (2013.01); *A61B 2018/00011* (2013.01); *A61B 2018/00029* (2013.01); *A61B 2018/00351* (2013.01); *A61B 2018/00357* (2013.01); *A61B 2018/00702* (2013.01); *A61B 2018/00744* (2013.01); *A61B 2018/00791* (2013.01); *A61B 2218/002* (2013.01); *A61M 2025/0063* (2013.01); *Y10T 29/49826* (2015.01)

(58) Field of Classification Search
CPC ............ A61M 25/0009; A61M 25/005; A61M 25/0054; A61M 2025/0063; A61B 18/1492; A61B 2018/00011; A61B 2018/00029; A61B 2018/00351; A61B 2018/00357; A61B 2018/00702; A61B 2018/00744; A61B 2018/00791; A61B 2218/002
USPC .......... 604/524, 525, 532, 523, 528
See application file for complete search history.

(56) References Cited

U.S. PATENT DOCUMENTS

| | | | | |
|---|---|---|---|---|
| 3,430,631 | A * | 3/1969 | Abramson | 604/541 |
| 4,950,259 | A * | 8/1990 | Geary et al. | 604/524 |
| 5,318,032 | A * | 6/1994 | Lonsbury et al. | 600/435 |
| 5,460,608 | A | 10/1995 | Lodin et al. | |
| 5,514,073 | A | 5/1996 | Miyata et al. | |
| 5,904,657 | A * | 5/1999 | Unsworth | A61M 25/0155 600/434 |
| 2005/0059957 | A1 * | 3/2005 | Campbell | A61M 25/0043 604/524 |
| 2005/0113660 | A1 * | 5/2005 | Fuimaono et al. | 600/374 |
| 2007/0088280 | A1 * | 4/2007 | Gomez | 604/174 |

(Continued)

FOREIGN PATENT DOCUMENTS

| | | |
|---|---|---|
| CN | 2658521 Y | 11/2004 |
| EP | 0 798 010 A1 | 10/1997 |

(Continued)

OTHER PUBLICATIONS

European Search Report dated Mar. 19, 2010 from corresponding European Patent Application No. 09252719.1.

(Continued)

*Primary Examiner* — Bhisma Mehta
*Assistant Examiner* — Brandy S Lee

(57) ABSTRACT

A medical device includes an insertion tube, having a distal end for insertion into a body of a subject and an opening at the distal end. A lumen, which includes a flexible tube which passes longitudinally through the insertion tube so as to communicate with the opening at the distal end of the insertion tube, is secured under tension inside the insertion tube.

4 Claims, 2 Drawing Sheets

(56) References Cited

U.S. PATENT DOCUMENTS

| | | |
|---|---|---|
| 2007/0156131 A1 | 7/2007 | Datta |
| 2007/0156132 A1* | 7/2007 | Drysen .......................... 606/41 |
| 2007/0282305 A1* | 12/2007 | Goldfarb et al. ............. 604/528 |
| 2009/0227962 A1* | 9/2009 | Eversull ................ A61L 29/085 |
| | | 604/265 |
| 2010/0152727 A1 | 6/2010 | Gibson et al. |

FOREIGN PATENT DOCUMENTS

| | | |
|---|---|---|
| EP | 1 736 184 A1 | 12/2006 |
| JP | 05-123403 A | 5/1993 |
| JP | 2007-537838 A | 12/2007 |
| WO | WO 2007/146995 A1 | 12/2007 |

OTHER PUBLICATIONS

Chinese First Office Action dated Jul. 23, 2012 from corresponding Chinese Patent Application No. 200910253602.7.
Japanese Notification of Reasons for Refusal dated Nov. 19, 2013 from corresponding Japanese Patent Application No. 2009-274174.

* cited by examiner

PREVENTION OF KINKS IN CATHETER IRRIGATION TUBES

FIELD OF THE INVENTION

The present invention relates generally to medical devices, and specifically to tubes that are used to convey fluids through invasive medical probes.

BACKGROUND OF THE INVENTION

In some medical procedures, energy is imparted to body tissue locally, in a concentrated dose, and it is desirable to cool the treatment area in order to reduce collateral tissue damage.

For example, cardiac ablation therapy is used to treat arrhythmias by heating tissue with radio-frequency (RF) electrical energy to create non-conducting lesions in the myocardium. It has been found that cooling the area of the ablation site reduces tissue charring and thrombus formation. For this purpose, Biosense Webster Inc. (Diamond Bar, Calif.) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

Catheter tubes are prone to kinking, and a number of methods for avoiding kinks are known in the art. For example, U.S. Pat. No. 5,460,608 describes a balloon catheter having an outer shaft and an inner shaft in which the inner shaft is constructed to protect itself over its entire length, especially in its most vulnerable areas, while maintaining flexibility. The inner shaft can be reinforced to prevent it from collapsing or breaking throughout its length and also improving the deflation time of the balloon.

SUMMARY OF THE INVENTION

The embodiments of the present invention that are described hereinbelow provide novel methods for assembling medical probes. These methods afford a simple, inexpensive way to produce probes with enhanced reliability and safety.

There is therefore provided, in accordance with an embodiment of the present invention, a medical device, including an insertion tube, having a distal end for insertion into a body of a subject and an opening at the distal end. A lumen, including a flexible tube which passes longitudinally through the insertion tube so as to communicate with the opening at the distal end of the insertion tube is secured under tension inside the insertion tube.

Typically, the lumen is configured to convey an irrigation fluid through the opening to tissue of the body in a vicinity of the distal end. In a disclosed embodiment, the device includes a distal tip made of a conductive material, which is disposed at the distal end of the insertion tube and is configured to contact and apply electrical energy to the tissue so as to ablate the tissue while the irrigation fluid cools the tissue.

There is also provided, in accordance with an embodiment of the present invention, a method for producing a medical device, including providing an insertion tube having a distal end for insertion into a body of a subject and an opening at the distal end. A flexible tube is inserted longitudinally through the insertion tube so as to communicate with the opening at the distal end of the insertion tube, and the flexible tube is fastened under tension inside the insertion tube.

In a disclosed embodiment, fastening the flexible tube includes bending the insertion tube to form a curve, and fixing the flexible tube within the insertion tube along an inner side of the curve.

The present invention will be more fully understood from the following detailed description of the embodiments thereof, taken together with the drawings in which:

DETAILED DESCRIPTION OF THE INVENTION

Figure 1:
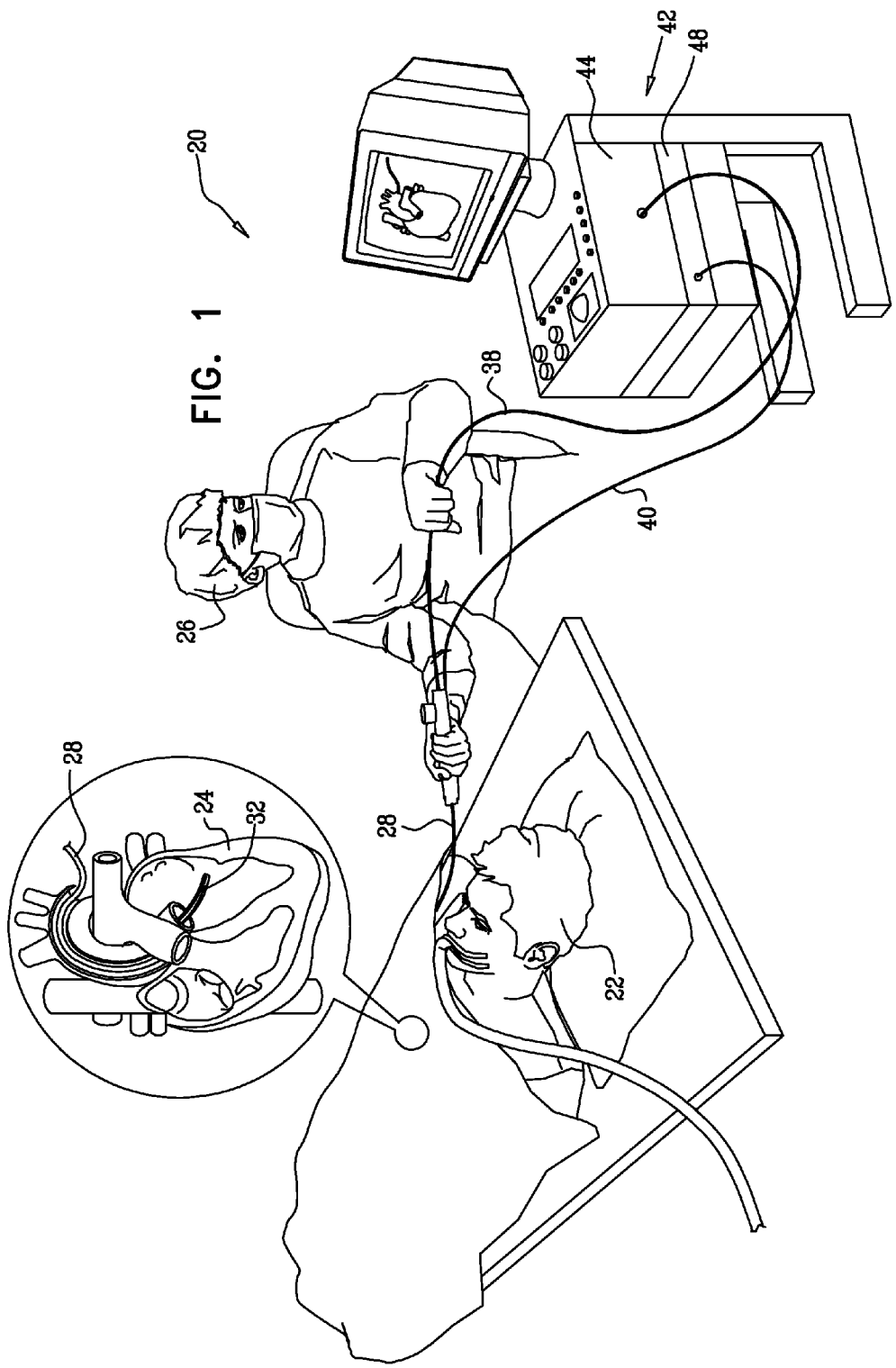
FIG. 1 is a schematic, pictorial illustration of a system for cardiac ablation therapy, in accordance with an embodiment of the present invention.

FIG. 1 is a schematic, pictorial illustration of a system 20 for cardiac ablation therapy, in accordance with an embodiment of the present invention. System 20 is shown here in order to provide an example of an environment in which the manufacturing techniques and device components that are described hereinbelow may be used. These techniques and components may likewise be applied, however, in other types of medical devices and systems.

An operator 26 of system 20 inserts a catheter 28 through a blood vessel into a chamber of a heart 24 of a subject 22, and manipulates the catheter so that a distal end 32 of the catheter contacts the endocardium in an area that is to be treated. The distal tip of the catheter has one or more openings to enable irrigation of the treatment area and a tensioned lumen for conveying irrigation fluid to the distal tip, as shown and described hereinbelow. In other respects, however, system 20 resembles systems for cardiac ablation treatment that are known in the art, such as the above-mentioned Biosense Webster system, and the components of such systems may be adapted for use in system 20.

After positioning distal end 32 at an ablation site, and ensuring that the tip is in contact with the endocardium at the site, operator 26 actuates a radio frequency (RF) energy generator 44 in a control console 42 to supply RF energy via a cable 38 to distal end 32. Meanwhile, an irrigation pump 48 supplies a cooling fluid, such as saline solution, via a tube 40 and the lumen in catheter 28 to the distal end. Operation of the RF energy generator and the irrigation pump may be coordinated in order to give the appropriate volume of irrigation during ablation, so as to cool the tip of the catheter and the tissue without overloading the heart with irrigation fluid. A temperature sensor (not shown in the figures) in distal end 32 may provide feedback to console 42 for use in controlling the RF energy dosage and/or irrigation volume.

Figure 2:
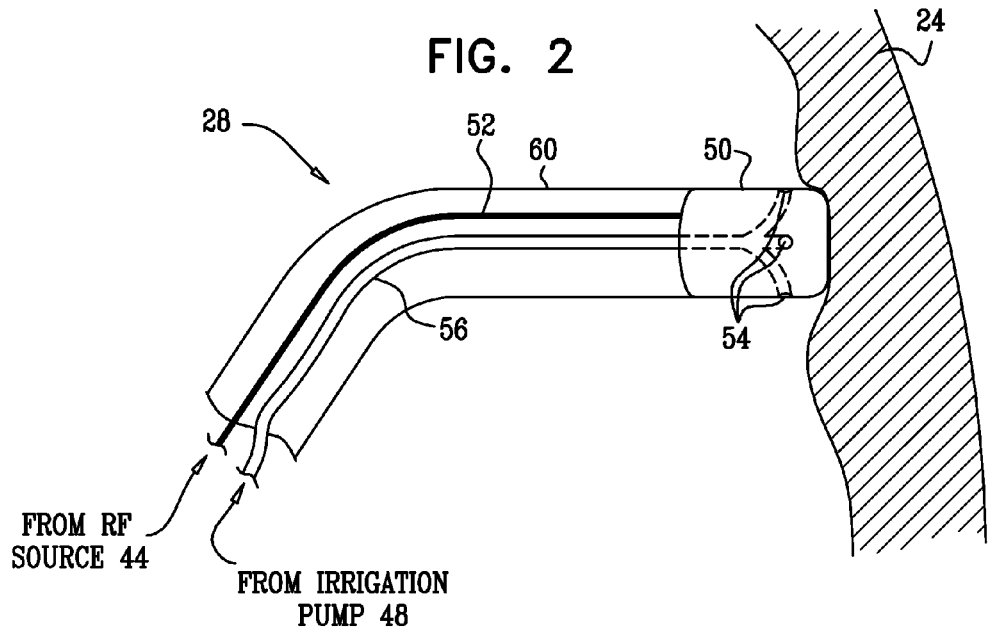
FIG. 2 is a schematic sectional view of the distal end of a catheter in engagement with heart tissue, in accordance with an embodiment of the present invention.

FIG. 2 is a schematic sectional view of distal end 32 of catheter 28 in engagement with endocardial tissue in heart 24, in accordance with an embodiment of the present invention. The catheter terminates in a distal tip 50, which is fixed to the distal end of an insertion tube 60 of the catheter. The distal tip typically comprises a conductive material, such as platinum, while the insertion tube has an insulating flexible outer sheath. An internal cable 52, which connects proximally to external cable 38 (FIG. 1), conveys RF energy to the distal tip in order to ablate the heart tissue.

The outer surface of distal tip 50 is penetrated by several openings 54. A lumen, in the form of a flexible irrigation tube 56 running longitudinally through insertion tube 60, conveys irrigation fluid from pump 48 and tube 50 to openings 54 in order to irrigate the tissue in the vicinity of the site that is being ablated. Although for the sake of simplicity, only a few openings 54 are shown in FIG. 2, a larger number of openings may be distributed over the surface of the distal tip both longitudinally and circumferentially.

Typically, in cardiac applications, insertion tube 60 has a diameter no greater than 3 mm. Irrigation tube 56 typically comprises a flexible plastic material, such as Polyimide. To fit inside insertion tube 60, and still leave room for cabling and other elements, the diameter of tube 56 is generally less than 1 mm (roughly 800 µm is typical), and its wall thickness is typically no more than about 60 µm. As a result, tube 56 is liable to kink and close off when the catheter bends, thus interrupting the flow of irrigation fluid, with potentially dire consequences.

In order to improve resistance to kinking of this sort, irrigation tube 56 is held under tension within insertion tube 60. This tension causes the wall of tube 56 to deform more evenly over its length when bent, relative to a flaccid tube, and therefore causes the tube to resist kinking unless catheter 28 is very sharply bent. The mechanical performance and safety of the fluid delivery lumen in catheter 28 are therefore enhanced.

Figure 3:
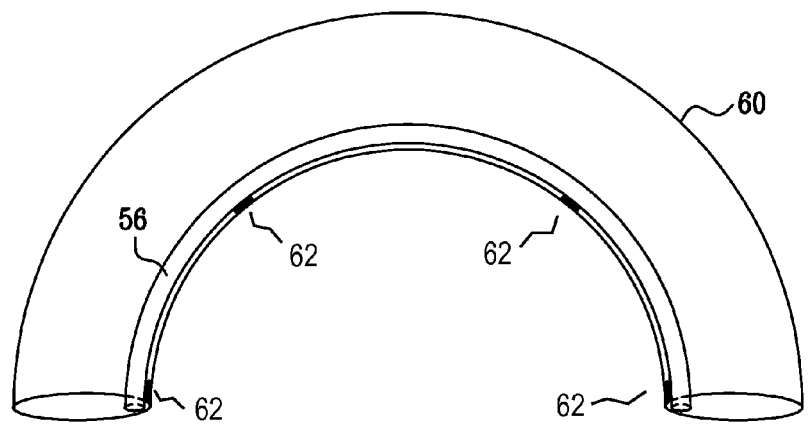
FIG. 3 is a schematic side view of a catheter, illustrating a method for assembling an irrigation tube within the catheter, in accordance with an embodiment of the present invention.

FIG. 3 is a schematic side view of insertion tube 60, illustrating a method for assembling irrigation tube 56 under tension within catheter 28, in accordance with an embodiment of the present invention. At the time of manufacture, irrigation tube 56 is inserted through insertion tube 60, and the insertion tube is bent into a curve, as shown in the figure. Irrigation tube 56 is then cemented against the inner side of the curve at two or more points (for example, at the distal and proximal ends), using a suitable adhesive 62, such as polyurethane cement. As a result, when catheter 28 is subsequently straightened, in its normal operating configuration, irrigation tube 56 will be under tension, without slack that could collapse when the catheter bends.

Although the technique illustrated in FIG. 3 provides a simple, convenient way to tension irrigation tube 56, other methods may be used for this purpose and are considered to be within the scope of the present invention. Furthermore, although the embodiment described above relates specifically to catheters used in RF ablation treatment within the heart, the principles of the present invention may similarly be applied to other organs and other types of probes and in other therapeutic and diagnostic modalities that involve delivery of fluid to or removal of fluid from body tissues.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for producing a medical device, comprising:
providing an insertion tube configured for insertion into a body of a subject, the insertion tube having a distal end with an opening at the distal end, and an inner wall;
inserting a flexible tube longitudinally through the insertion tube so as to communicate with the opening at the distal end of the insertion tube;
bending the insertion tube to form a curve;
fastening the flexible tube under tension directly to the inner wall of the insertion tube while the insertion tube is bent, the flexible tube being secured under tension to the insertion tube, the flexible tube being secured under tension in any position of the insertion tube including when the insertion tube is substantially straight; and
locating an adhesive on the flexible tube and the inner wall of the insertion tube at two or more locations in spaced relation to each other for securing the flexible tube to the inner wall of the insertion tube.

2. The method according to claim 1, wherein fastening the flexible tube comprises fixing the flexible tube within the insertion tube along the inner wall of the curve.

3. A method for providing a flexible tube under tension within an insertion tube, comprising:
providing an insertion tube having a distal end for insertion into a body of a subject and an opening at the distal end;
inserting a flexible tube longitudinally through the insertion tube such that the flexible tube communicates with the opening at the distal end of the insertion tube;
bending the insertion tube to form a curve;
fastening the flexible tube under tension directly to an inner wall of the insertion tube while the insertion tube is in a curved shape such that the flexible tube is secured under tension, the flexible tube being secured under tension in any position of the insertion tube including the insertion tube being substantially straightened; and
locating an adhesive on the flexible tube and the inner wall of the insertion tube at two or more locations in spaced relation to each other for securing the flexible tube to the inner wall of the insertion tube.

4. The method of claim 3, further comprising:
Maintaining the tension of the flexible tube secured to the inner wall of the insertion tube when the insertion tube is in a plurality of positions including a substantially straight position.

* * * * *